US010973659B2

(12) United States Patent
Cabot

(10) Patent No.: US 10,973,659 B2
(45) Date of Patent: Apr. 13, 2021

(54) ARRANGEMENT AND METHOD USED IN THE PREPARATION OF THE PROXIMAL SURFACE OF THE TIBIA FOR THE TIBIA COMPONENT OF A PROSTHETIC KNEE JOINT

(71) Applicant: Jonathan Peter Cabot, North Adelaide (AU)

(72) Inventor: Jonathan Peter Cabot, North Adelaide (AU)

(*) Notice: Subject to any disclaimer, the term of this patent is extended or adjusted under 35 U.S.C. 154(b) by 303 days.

(21) Appl. No.: 16/094,035

(22) PCT Filed: Apr. 20, 2017

(86) PCT No.: PCT/AU2017/000092
§ 371 (c)(1),
(2) Date: Oct. 16, 2018

(87) PCT Pub. No.: WO2017/181216
PCT Pub. Date: Oct. 26, 2017

(65) Prior Publication Data
US 2019/0110905 A1 Apr. 18, 2019

(30) Foreign Application Priority Data

Apr. 22, 2016 (AU) .............................. 2016901499

(51) Int. Cl.
| A61F 2/46 | (2006.01) |
| A61B 17/15 | (2006.01) |
| A61B 17/17 | (2006.01) |
| A61F 2/38 | (2006.01) |
| A61B 17/02 | (2006.01) |
| A61F 2/30 | (2006.01) |
| A61B 90/00 | (2016.01) |
| A61B 17/00 | (2006.01) |

(52) U.S. Cl.
CPC .......... *A61F 2/4684* (2013.01); *A61B 17/025* (2013.01); *A61B 17/157* (2013.01);
(Continued)

(58) Field of Classification Search
CPC ........ A61F 2/46; A61F 2/4657; A61F 2/4684; A61F 2/38; A61F 2/3859; A61F 2/3868;
(Continued)

(56) References Cited

U.S. PATENT DOCUMENTS 5,733,292 A * 3/1998 Gustilo ................ A61B 17/025
606/86 R
7,104,996 B2 * 9/2006 Bonutti .............. A61B 17/1735
606/86 R
(Continued)

FOREIGN PATENT DOCUMENTS

EP 2918235 4/2017
WO 2011128657 10/2011
(Continued)

*Primary Examiner* — Jessica Weiss
(74) *Attorney, Agent, or Firm* — Renner Kenner Greive Bobak Taylor & Weber

(57) ABSTRACT

An arrangement for the preparation of the proximal surface of the tibia for a tibia component of a prosthetic knee joint, wherein the arrangement includes a preparation plate that assists in defining a reference plane. A cutting guide arrangement includes an indicator that provides orientation for a cutting blade or saw to cut the final bone resection of the proximal surface of the tibia the same as the reference plane. There is also a mounting arrangement between the joint liner and the cutting guide arrangement, so that in a first mounting position the indicator of the cutting guide is aligned with the same referenced plane defined by the underside of the joint liner and wherein the mounting arrangement also provides a second mounted position wherein the indicator of the cutting guide is aligned with the same referenced plane orientation of the underside of the joint liner but below the initial resected proximal surface of the tibia where the final resection of bone will take place.

10 Claims, 10 Drawing Sheets

(52) U.S. Cl.
CPC ................. *A61F 2/38* (2013.01); *A61F 2/46* (2013.01); *A61F 2/4657* (2013.01); *A61B 2017/00367* (2013.01); *A61B 2017/00407* (2013.01); *A61B 2017/00539* (2013.01); *A61B 2017/00544* (2013.01); *A61B 2090/061* (2016.02); *A61F 2/389* (2013.01); *A61F 2002/30556* (2013.01); *A61F 2002/4661* (2013.01)

(58) Field of Classification Search
CPC ............ A61F 2/389; A61F 2002/30556; A61F 2002/4661; A61B 17/025; A61B 17/157; A61B 2090/061; A61B 2017/00367; A61B 2017/00407; A61B 2017/00539; A61B 2017/00544
USPC ...... 606/87–90, 86 R, 82, 96–99; 623/20.32, 623/20.35
See application file for complete search history.

(56) References Cited

U.S. PATENT DOCUMENTS

| | | | | |
|---|---|---|---|---|
| 7,635,369 | B2 * | 12/2009 | Cinquin | A61B 17/025 606/90 |
| 8,337,508 | B2 * | 12/2012 | Lavallee | A61B 90/36 606/105 |
| 9,592,133 | B2 * | 3/2017 | Toler | A61B 17/025 |
| 2005/0020941 | A1 | 1/2005 | Tarabichi | |
| 2012/0158152 | A1 * | 6/2012 | Claypool | A61F 2/3868 623/20.33 |
| 2013/0102929 | A1 * | 4/2013 | Haight | A61F 2/4657 600/587 |
| 2014/0052269 | A1 * | 2/2014 | Claypool | A61F 2/4684 623/20.33 |
| 2014/0296859 | A1 * | 10/2014 | Claypool | A61F 2/4684 606/88 |
| 2015/0088140 | A1 * | 3/2015 | Toler | A61B 17/025 606/88 |
| 2015/0230804 | A1 * | 8/2015 | Ghana | A61B 17/025 606/88 |
| 2015/0374388 | A1 | 12/2015 | Aram et al. | |
| 2016/0324647 | A1 * | 11/2016 | Claypool | A61B 5/1036 |
| 2016/0346098 | A1 * | 12/2016 | Uthgenannt | A61F 2/389 |
| 2017/0105848 | A1 * | 4/2017 | Wogoman | A61B 17/1604 |

FOREIGN PATENT DOCUMENTS

| | | |
|---|---|---|
| WO | 2012020460 | 2/2012 |
| WO | 2016065396 | 5/2016 |

* cited by examiner

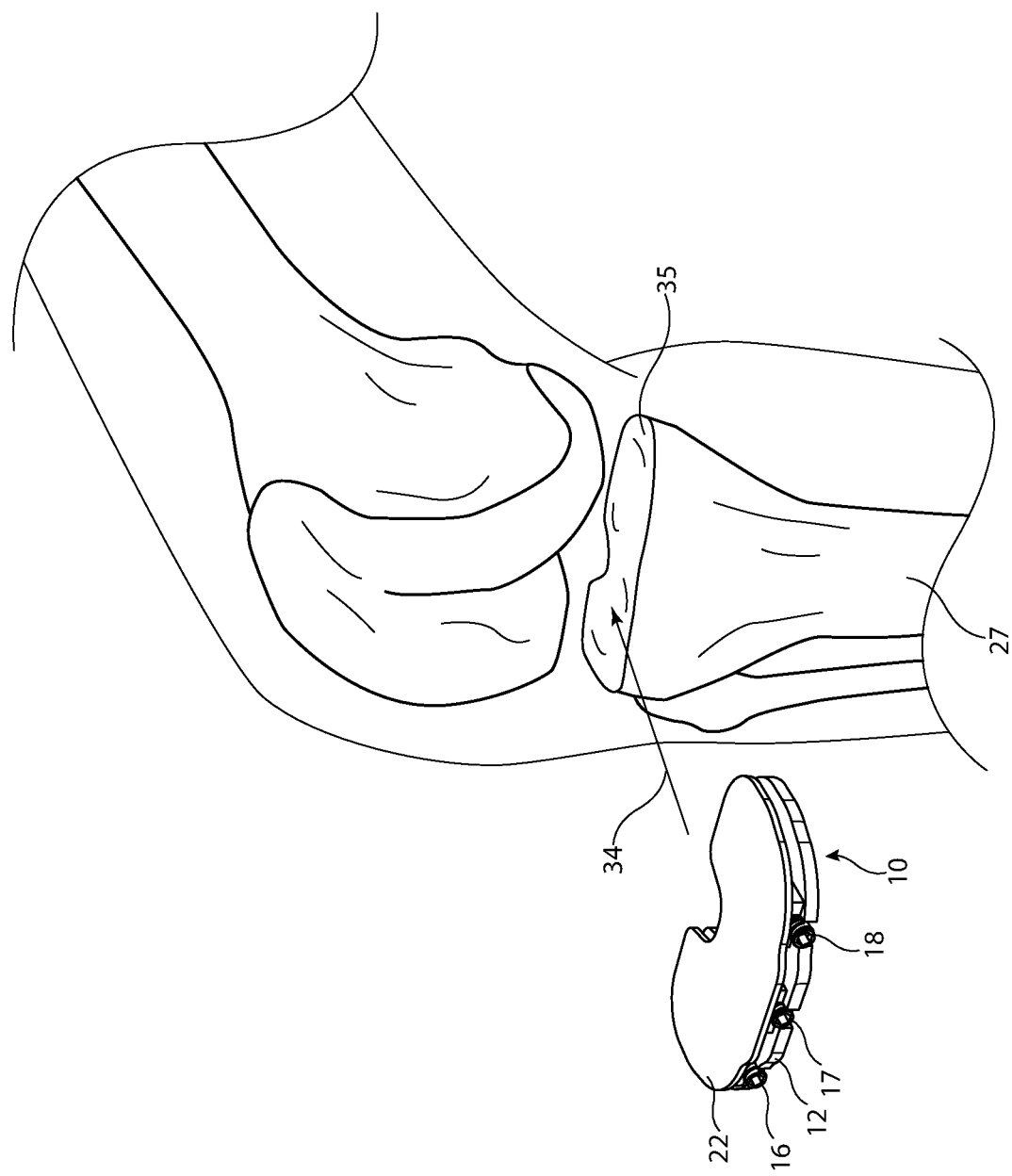

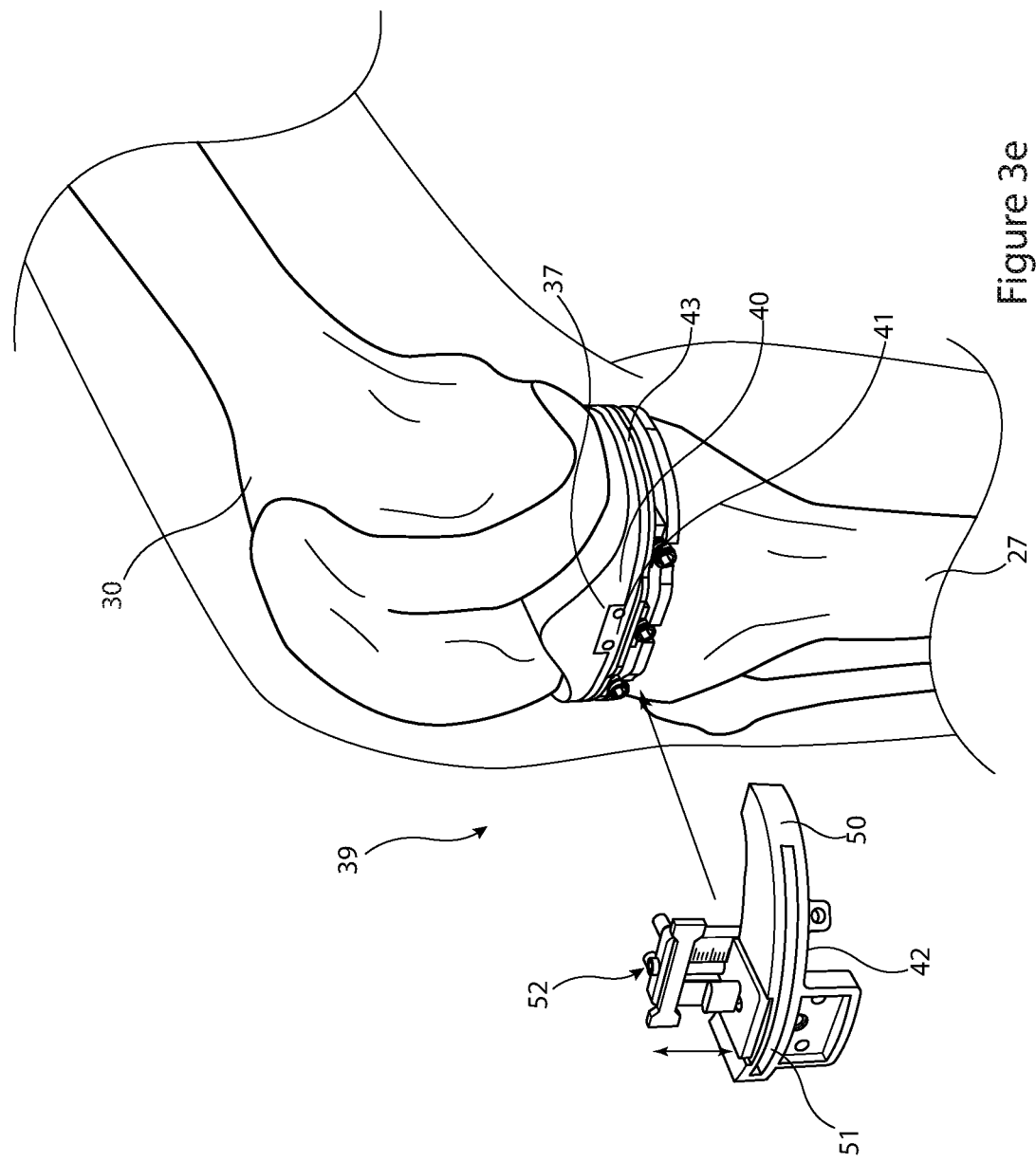

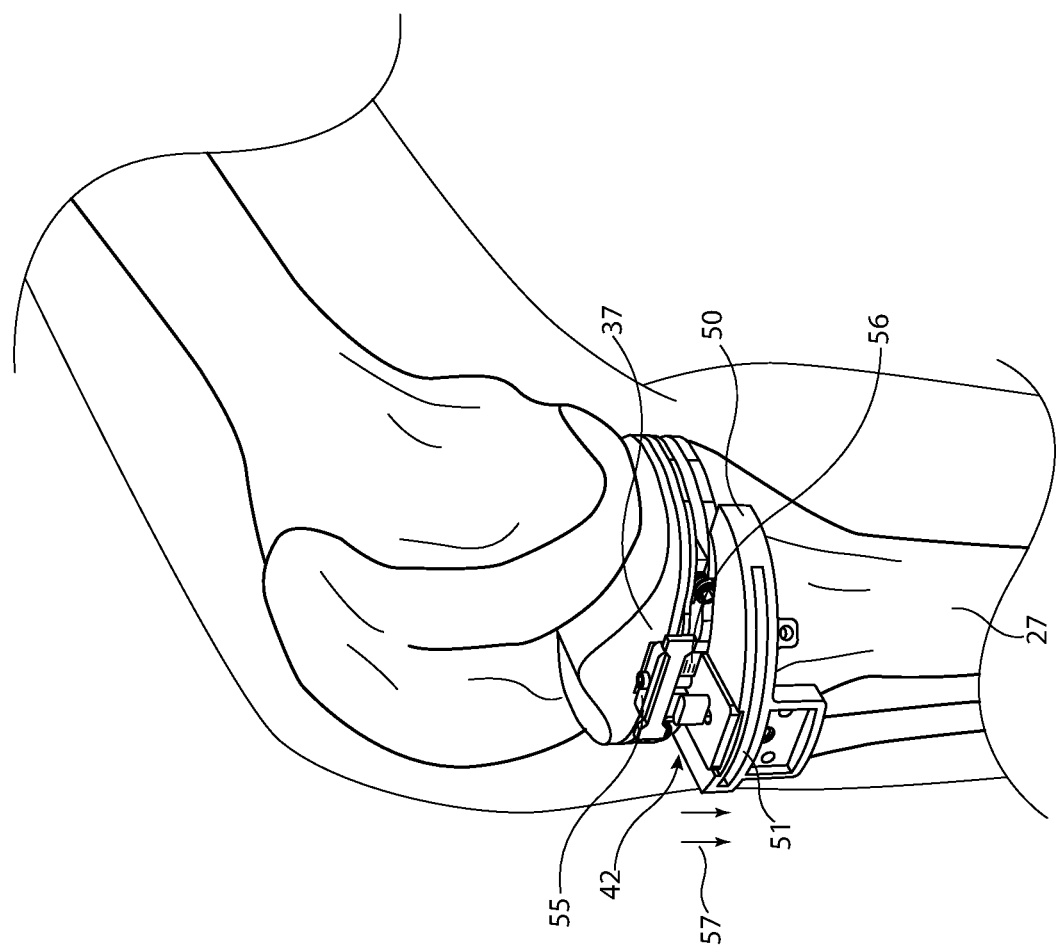

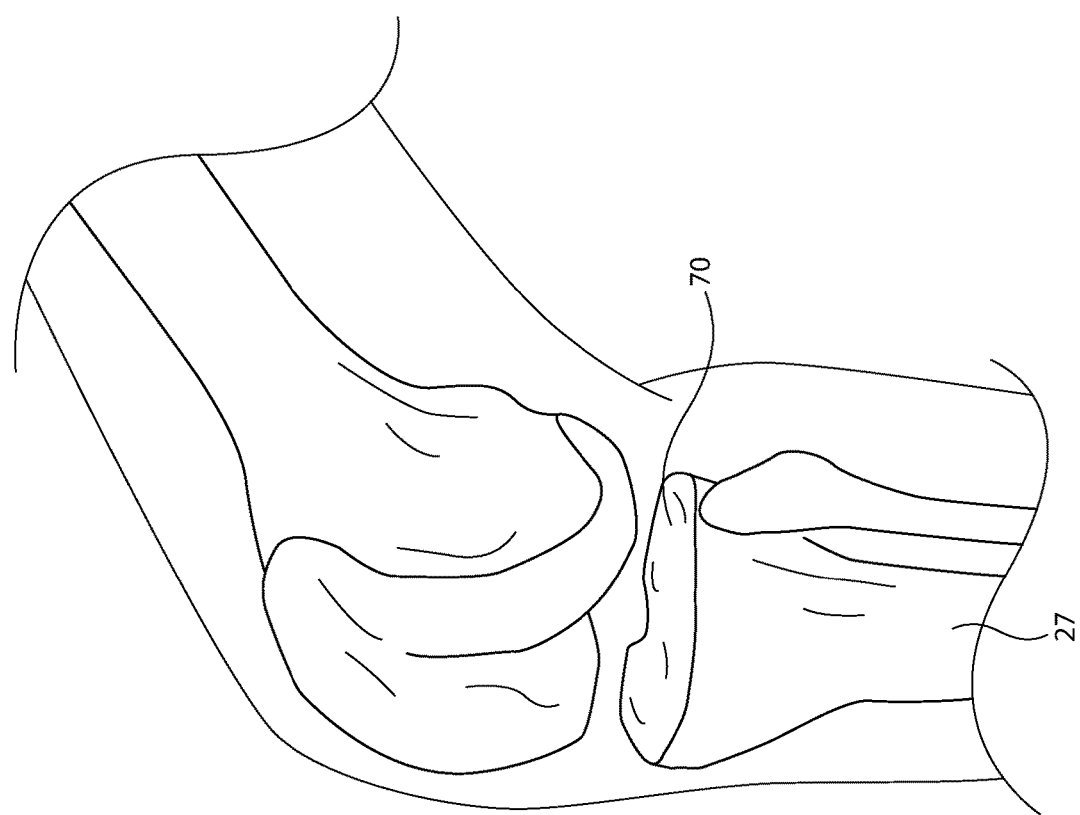

ARRANGEMENT AND METHOD USED IN THE PREPARATION OF THE PROXIMAL SURFACE OF THE TIBIA FOR THE TIBIA COMPONENT OF A PROSTHETIC KNEE JOINT

TECHNOLOGICAL FIELD

This invention relates to an improved arrangement and method in the preparation of the proximal surface of the tibia for the tibia component of a prosthetic knee joint.

More particularly this invention relates to the preparation of the proximal surface of the tibia such that the level and/or profiling of the final bone resection on the proximal surface of the tibia is such so as to provide balanced stability between the tibia component and/or the femoral component of the prosthetic knee joint to permit stable and balanced movement of the knee joint through its angular movement from extension, mid flexion and through to flexion and then back again.

BACKGROUND OF DISCUSSION

Referencing throughout this specification while for the most part has been described is the preparation of the complete proximal surface of the tibia for a total knee replacement, the scope of the invention to be describe and to be defined is also intended to encompass uni-compartmental knee replacements wherein portions of the knee joint, such as a half, require prosthetics.

The applicant hitherto as disclosed in the applicant's earlier international PCT application PCT/AU2015/000643 was able to provide for an arrangement and a method such that the proximal surface of the tibia or profile of the final bone resection of the surface of the tibia provides for optimum tibia component positioning in knee arthroplasty such there is a stable and balanced movement between the tibia component of the prosthetic knee joint throughout the complete arc of motion of the knee from extension to mid-flexion to flexion.

The ability to achieve this favourable outcome relied upon an arrangement that utilised an adjustable tibia and femoral preparation plate, stability gap guide drill plate and then finally a stability gap router plate. Hence previously there was the requirement to establish a stability gap, complete a drilling step and then ultimately routing before the final tibia bone resection was complete.

Using the applicant's earlier invention once the tibia and femoral stability gap preparation plate determined a suitable stability gap by the user adjusting the height adjustability of each of the extension tabs of the tibia and femoral stability gap preparation plate, this relative height (now depth in the context of the resection into the surface of the tibia) then needs to be resected off the proximal surface of the tibia in order to establish the overall profile of the proximal surface of the tibia for the tibia component to rest thereupon.

The applicant has found that whilst the stability gap drill plate and then use of the stability gap router plate ultimately provided for the requisite profile of the surface of the tibia to provide optimum tibia component positioning in the knee arthroplasty, including both total and uni-compartmental knee replacements, the implementation and use of the stability gap guide drill plate and the stability gap router plate in order to achieve final bone resection is potentially cumbersome, time consuming, open to error as there are too many steps, and if skills are not employed could result in not correctly establishing the final bone resection based on the originally defined stability gap provided for by the tibia and femoral stability gap preparation plate.

Whilst the applicants previous invention through the use of the tibia and femoral preparation plate could determine and define the suitable gap for balanced knee joint movement post patient operation, the stability guide drill plate and the stability gap router plate required to many further steps and use of too much specialized apparatus and skill for those carrying out the operation in order to achieve that requisite profile of the proximal surface of the tibia.

Given that for the most part the significance of the applicant's earlier invention was the realization of being able to make a available a tibia and femoral stability preparation plate to find the suitable gap that would be required for the tibia and femoral component, it would be advantageous to be able to come up with an improved and refined arrangement and method that could more easily translate the results obtained by the tibia and femoral stability gap preparation plate in order to conveniently, safely, consistently and without necessarily additional specialized skills that other wise would be required to make sure that the defined suitability gap established by the tibia and femoral gap preparation plate ultimately and correctly results in the requisite profile of the proximal surface of the tibia once the fine bone resection of the tibia is completed.

Accordingly, it is an object of this invention to provide an improved arrangement and method that once the tibia and femoral stability gap preparation plate has determined and been able to define a stability gap that would be required for the tibia component and the femoral component for balanced and stable knee joint movement, this measurement of the stability gap would be more conveniently, safely and consistently thereafter translated into simplified steps to complete the requisite profile of the proximal surface of the tibia through the fine bone resection.

Further objects and advantages of the invention will become apparent when reading the following specification.

SUMMARY OF THE INVENTION

In one form of the invention there is provided an arrangement for the preparation of the proximal surface of the tibia for a tibia component of a prosthetic knee joint, said arrangement including:

a tibia and femoral stability gap preparation plate, said tibia and femoral stability gap preparation plate adapted to be placed upon an initially resected proximal surface of the tibia, said tibia and femoral stability gap preparation plate further including an upper side, said upper side having a plurality of user operable height adjustable extension tabs, wherein each user operable height adjustable extension tab is adapted to engage an underside of a joint liner, wherein said joint liner includes an upper articulated surface to engage a femoral component of a knee joint, such that a height adjustment of said plurality of user operable height adjustable extension tabs defines a stability gap as a measurement taken in each of extension, mid-flexion and flexion, wherein the stability gap is commensurate with a reference plane defined on an underside of the joint liner, wherein a final bone resection of the proximal surface of the tibia consistent with said reference plane provides for balanced angular movement between the tibia component and the femoral component of a prosthetic knee joint throughout an arc of motion from extension, mid-flexion and flexion;

a final bone resection of the proximal surface of the tibia cutting guide arrangement, said final bone resection of the proximal surface of the tibia cutting guide arrangement including a cutting guide having an indicator, wherein the indicator provides a reference guide for a cutting blade or saw to cut the final bone resection of the proximal surface of the tibia;

said joint liner and said final bone resection of the proximal surface of tibia cutting guide arrangement including a mounting arrangement, wherein the mounting arrangement is configured to provide a first mounted position between said joint liner and said final bone resection of the proximal surface of tibia cutting guide arrangement, wherein the indicator of the cutting guide is aligned with the same referenced plane as the referenced plane defined by the underside of the joint liner;

said mounting arrangement further configured to provide a second mounted position wherein the indicator of the cutting guide aligned with the same referenced plane of the underside of the joint liner is adjustable below the initial resected proximal surface of the tibia.

Advantageously, this invention has provided a much more consistent, convenient and safe reproducible arrangement and method for establishing the appropriate final resection for the proximal surface of the tibia, such that there will be a stable balanced angular movement between the tibia component and the femoral component of the prosthetic knee joint throughout an arc of motion from extension, mid-flexion and flexion post surgery for the patient.

Previously, the stability gap while providing a guide as to how the proximal surface of the tibia needed to be profiled to obtain optimum preparation of the prosthetic knee joint, it also involved a complicated way in which to make the final resection cut.

Firstly a stability gap guide drill plate to drill the hole to a depth that has been identified by the height adjustment of each of the respective extension tabs that were adjusted by the user when the tibia and femoral stability gap preparation plate was placed upon the initial resected box on the surface of the tibia, meant that one had to drill down to a commensurate level with the adjusted height of each of the respective extension tabs and once the stability gap drill plate was withdrawn, there was then a requirement of trying to complete the final bone resection, wherein a stability router plate would have to be used, in order to level off the proximal surface of the tibia about the drilled bone holes.

Rather than using the conventional cutting blade or saw this stability gap router plate had to include a series of vertical mounts which would engage the bore holes drilled into the proximal surface of the tibia through the stability gap guide drill plate step. The router would then need to complete the bone resection, so that all the bone could be cut down to the depth of each of the boreholes, to again ultimately provide that required profiled surface.

Advantageously, this invention through the improved arrangement however has simplified the process. By recognizing the significance of the stability gap and then using this measurement and translating that to a 'reference plane' defined by the orientation of the underside of the joint liner this referenced plane when replicated as a final bone resection cut in the bone under the initial resection cut of the proximal surface of the tibia provides the necessary surface profile that when the tibia component of the prosthetic knee joint is implanted in the knee joint of the patient, it would be configured as to enable balanced stability between the tibia and femoral components of the prosthetic knee joint, whether that be a uni-compartmental knee replacement or a total knee replacement.

Once the tibia and femoral stability gap preparation plate through the user operable height extension tabs have established that reference plane by engagement of the underside of the joint liner, the mounting arrangement then has the means in which this reference plane can be replicated in that new bone below the initially resected proximal surface of the tibia.

In the establishment of the first mounted position, the engagement between the joint liner and the final bone resection of the proximal surface of the tibia cutting arrangement is such so that the indicator of the cutting guide has been aligned to replicate that same alignment or profile as the reference plane of the underside of the joint liner.

However, just having the requisite alignment of the indicator is still not enough to complete the final resected cut and the indicator needs to be lowered after the initial mounting position in the first mounted position so the indicator is position where there is new bone below the initial resection made to the bone of the proximal surface of the tibia, as that new bone to be cut in the final resection will have the necessary structural integrity to support the components of the prosthetic knee joint.

In preference the mounting arrangement is configured to provide the first mounted position between the tibia and femoral stability gap preparation plate by at least one slot and at least a corresponding lug.

In preference the joint liner includes at least one slot and the final bone resection of the proximal surface of the tibia cutting guide arrangement includes a or corresponding lug for the or each slot or wherein the joint liner includes at least one lug and the final bone resection of the proximal surface of the tibia cutting guide arrangement includes a or corresponding slot for the or each lug.

In preference there are at least a pair of slots on the front side of the joint liner and a pair of corresponding lugs protruding out from the front of the final bone resection of the proximal surface of the tibia cutting guide arrangement or wherein there are at least a pair of lugs protruding out a front side of the joint liner and a pair of corresponding slots in the final bone resection of the proximal surface of the tibia cutting guide arrangement.

In preference the mounting provides the second mounted position by including a vertical support, wherein the vertical support allows the cutting guide to be vertically adjustable there along said vertical support.

In preference the vertical support is adapted to incrementally adjust and position the cutting guide vertically there along said vertical support.

In preference the vertical incremental adjustment of the cutting guide along the vertical support includes a ratchet arrangement.

In further embodiments of the invention the vertical incremental adjustability of the cutting guide along the vertical support can include a clutch, intermediate gearing and cams.

In preference the indicator of the cutting guide includes a slot where in a saw or blade to complete the final bone resection of the proximal surface of the tibia is guidable into said slot of the indicator of the cutting guide so as to orientate the saw or blade to cut the proximal surface of the tibia with a commensurate profile to the established reference plane on the underside of the joint liner.

In preference the tibia and femoral gap preparation plate includes three operable height adjustable extension tabs, wherein raisable tips of each operable height adjustable extension tab, when said tips are raised define a plane configurable from each of the raised tips, wherein the defined plane is commensurate with the reference plane defined by the height adjusted position of the underside of the joint liner.

In preference each operable height adjustable extension tab is in communication with a corresponding user engagable knob.

In preference the adjustable tabs utilize a mechanical, hydraulic, electrical, electronic and/or pneumatic drive action.

Advantageously the plane of plate can be adjusted to an infinite number of positions in 3D to get the perfect resection plane for the balanced knee joint. And wherein further the height of adjustable tabs allows 3D movement of the plate.

In order now to describe the invention in greater detail a series of the preferred embodiments of the invention will be shown with the assistance of the following illustrations and accompanying text.

BRIEF DESCRIPTION OF THE DRAWINGS

FIGS. 1a and 1b show perspective views of the tibia and femoral stability gap preparation plate in a preferred embodiment of the invention wherein FIG. 1a shows the user operable extension tabs in a lowered position wherein FIG. 1b shows the user operable extension tabs in adjusted raised positions.

DETAILED DESCRIPTION OF THE DRAWINGS

Figure 1:
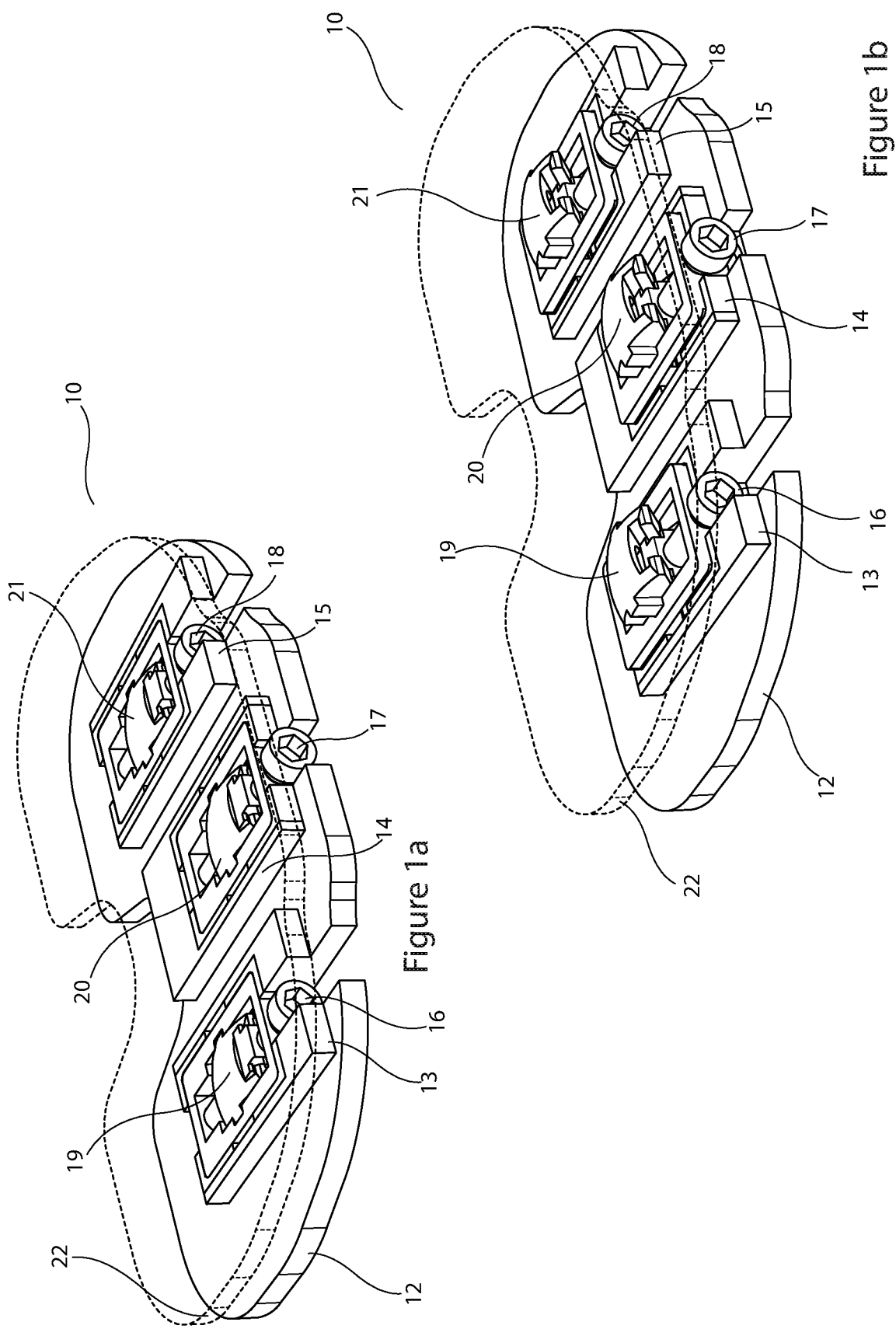

Referring to the drawings now in greater detail wherein the tibia and femoral stability gap preparation plate which forms part of the overall arrangement of the preparation of the proximal surface of the tibia or a tibia component of a prosthetic knee joint for this invention is referenced generally as 10.

Figure 2:
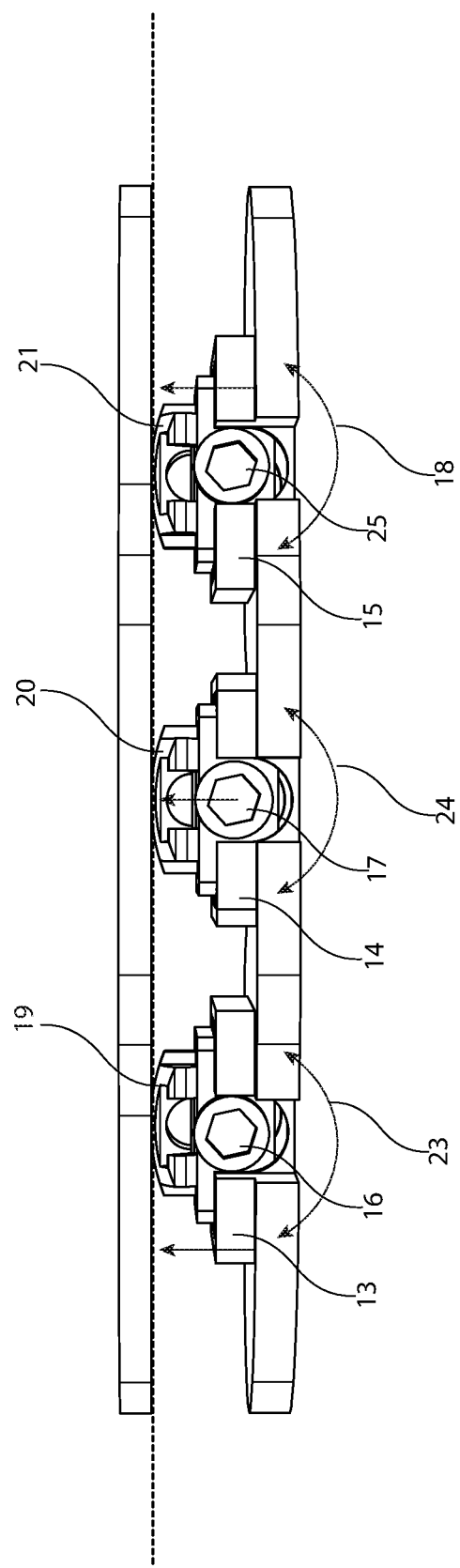
FIG. 2 is a front view of the tibia and femoral stability gap preparation plate in a preferred embodiment of the invention.
Figure 3A:
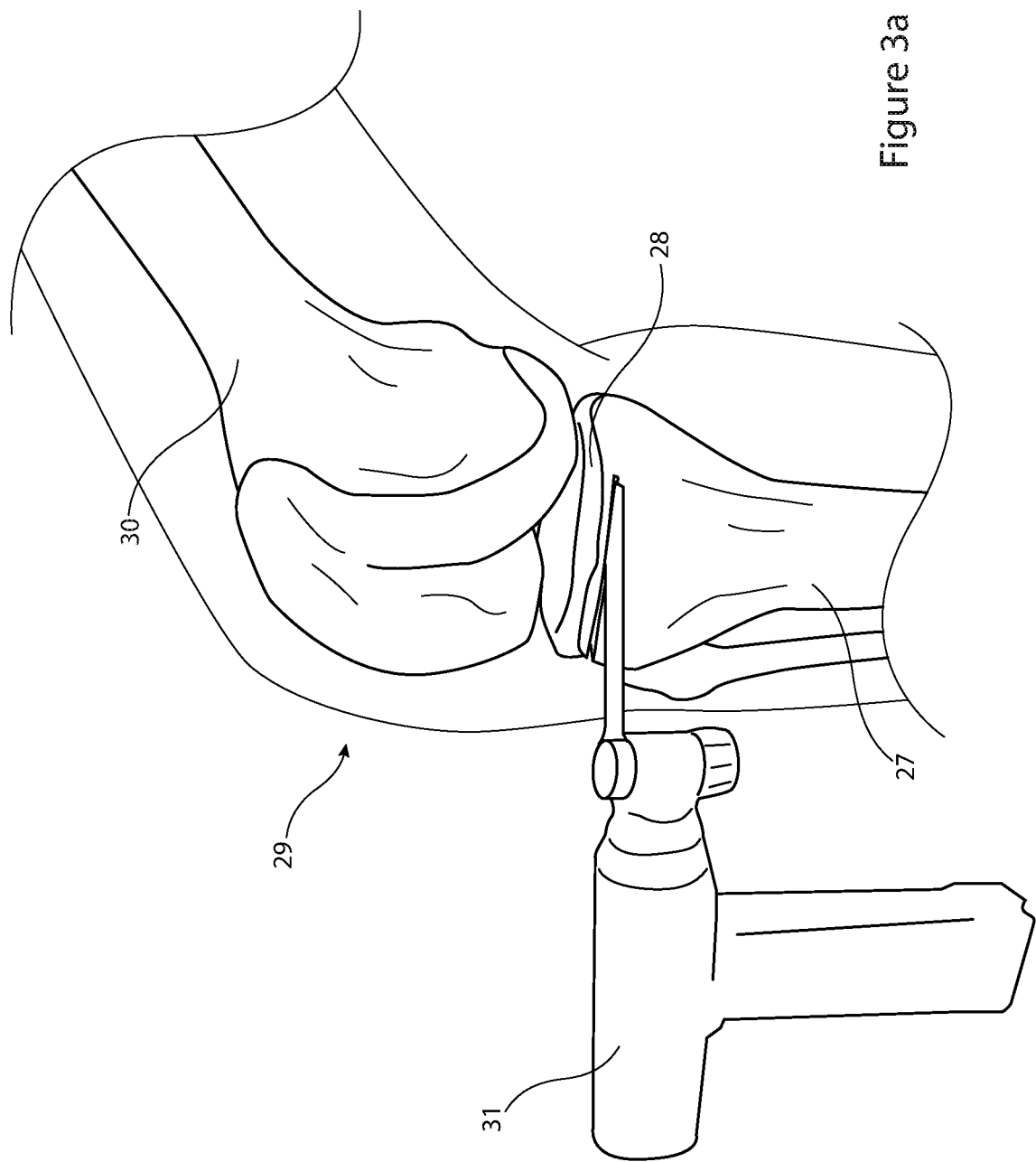
FIGS. 3a through to 3h are schematic representations showing the use of the arrangement for the preparation of the proximal surface of the tibia for the tibia component of a prosthetic knee joint.

The tibia and femoral stability gap preparation plate 10 in the preferred embodiment shown in FIGS. 1a, 1b and FIG. 2, includes a base plate 12, which we will discuss in greater detail on FIGS. 3a through to 3h.

The base plate 12 is configured to rest appropriately upon the initial cut proximal surface of the tibia.

In the preferred embodiment shown in FIGS. 1a, 1b and 2, there is also included the top plate or platform 22 shown in broken lines in FIGS. 1a and 1b. However, the user operable height adjustable extension tabs 13, 14 and 15 and the associated tip 19, 20 and 21 can also directly engage the underside 43 of the joint liner 37, again as to be discussed in greater detail when referencing FIGS. 3a to 3h, in the preferred embodiments the top plate 22 will engage the underside 43 of the joint liner 37.

The user operable height adjustable extension tabs 13, 14 and 15 are in operable engagement with the rotatable knobs 16, 17 and 18. As referenced by arrows 23, 24 and 25 rotations of rotatable knobs 16, 17 and 18 translates to the vertical height adjustment of the tips 19, 20 and 21 of the corresponding user operable height adjustment extension tabs 13, 14 and 15.

FIG. 1a shows tips 19, 20 and 21 of the user operable extension tabs 13, 14 and 15 in a lowered position and in FIG. 1b rotational movement of the user enagable knobs 16, 17 and 18 has seen the elevated height of the tips 19, 20 and 21 of the corresponding height adjustable extension tabs 13, 14 and 15 raised which is representative of their adjustability in order to establish the stability gap during the appropriate adjustment as to be discussed in greater detail when referencing FIGS. 3a through to 3h.

By having three tips 19, 20 and 21 this provides for a triangulation which is establishing an appropriate reference plane upon the plate 22 which will be discussed in greater detail in referencing FIGS. 3a through to 3h will then be translated to the orientation of the underside 43 of the joint liner 37, to which plate 22 of the tibia and femoral stability gap preparation plate 10 engages.

In relation to FIGS. 3a through to 3h the illustrations need to be placed in the context of the intended outcome achieved through the use of arrangement and methods provided for in this invention.

Orthopaedic surgeons during surgery aim to provide balance, unobstructed movement of the knee components for the complete arc of motion from extension, mid-flexion and flexion and then back again.

Accordingly, the final bone resection of the proximal surface of the tibia is required to be cut correctly in order to present the appropriate profile to the tibia component positioning in the knee anthroplasty whether that be a total knee or uni-compartmental knee operation.

FIG. 3a shows a knee joint generally as 29.

A cutter 31, prepares for the initial resection of the proximal surface 28 of the tibia 27. The general distal end of the femur 30 is also shown. In FIG. 3b the tibia and femoral stability gap preparation plate 10 shown by way of arrow 34 is being inserted onto the initially resected proximal surface 35 of the tibia 27.

From FIG. 3b it can realise that the general shape of the tibia and femoral stability gap preparation plate 10 is of a comparative dimension of the proximal surface 35 of the tibia 27.

Figure 3C:
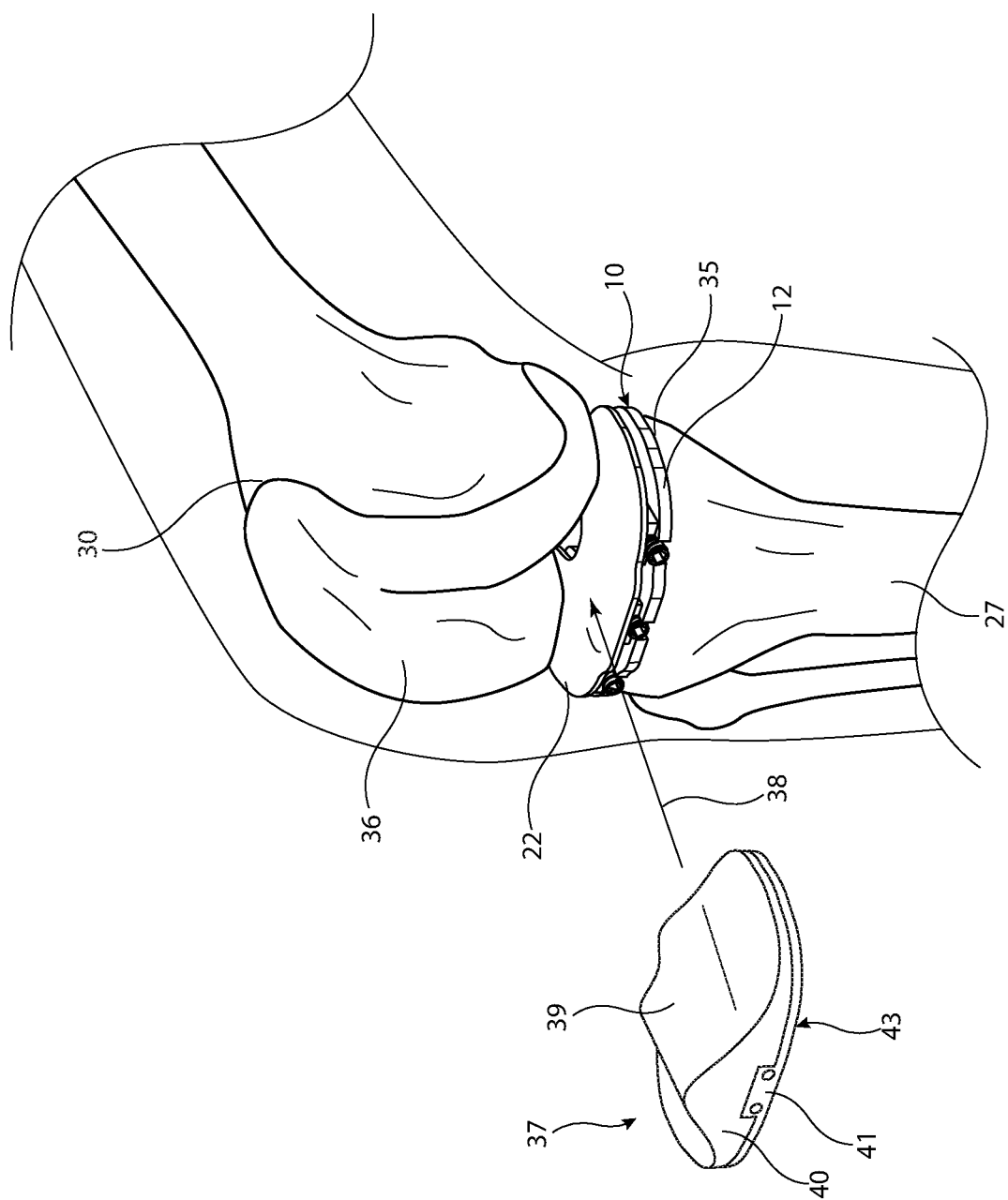

FIG. 3c shows the actual positioning of tibia and femoral stability gap preparation plate 10 on the proximal surface 35 of the tibia 27 and to be sandwiched therein between the femoral component 36 and the tibia and femoral stability gap preparation plate 10 is the joint liner 37.

Arrow 38 is representative as to the location the joint liner 37 will be positioned in the knee joint 29.

The joint liner 37 has an articulated upper surface 39 to engage the femoral component 36 of the femur 30.

Importantly, the joint liner 37 on the front side 40 includes a pair of slots 41 of which will be discussed in greater detail when referencing the mounting arrangement between the joint liner 37 and the final bone resection proximal surface of the tibia cutting guide arrangement 42 which is introduced in FIG. 3e.

43 is representative of the under side of the joint liner 37.

Figure 3D:
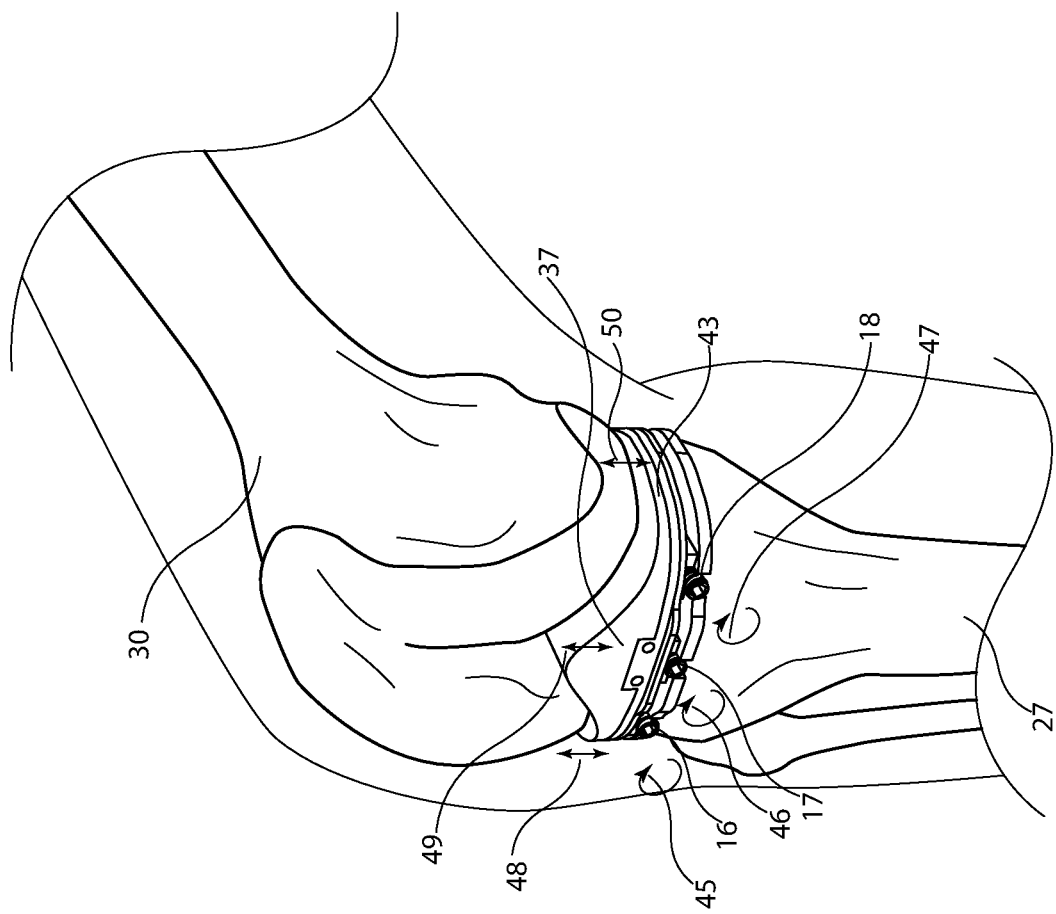

FIG. 3d shows the knee joint at mid-flexion. Operable knobs 16, 17 and 18 when rotated by way of arrows 45, 46 and 47 though the height adjustable extension tabs, 13, 14 and 15 will adjust the orientation of the underside 43 of the joint liner 37.

This height adjustability although not shown in the illustrations would also have been completed at extension and then ultimately at flexion or 90 degrees.

Accordingly, the user operable height adjustable extension tabs 13, 14 and 15 create a triangular support of the top plate 22, which then aligns and/or orientates the underside 43 of the joint line 37 accordingly. The stability gap that has been established is commensurate with the references plane that has now been established on the underside 43 of the joint liner 37 through the height adjustability of the height adjustable extension tabs 13, 14 and 15 from extension, mid-flexion and flexion.

Hence albeit the tibia and femoral stability gap preparation plate 10 provides for a stability gap, this stability gap is then represented by the referenced plane now provided for on the underside 43 of the joint liner 37.

With the referenced plane now established on the underside 43 of the joint liner 37, the final bone resection of the proximal surface of the tibia cutting guide arrangement is then mountable to the joint liner 37.

The final bone resection of the proximal surface of the tibia cutting guide arrangement 42, as best seen in FIG. 3e, includes a cutting guide 50, wherein the cutting guide 50 includes an indicator in the form of a slot 51.

The purpose of the slot 51 is that it will allow the blade or a saw to be guided to make a final resection cut of the proximal surface of the tibia in the orientation as to the alignment of the slot.

It is therefore a requirement that the indicator, which in this preferred embodiment is a slot 51 included as part of the cutting guide 50 is aligned the same as the underside 43 of the joint liner 37 so as to make sure that the profile provided for by the final bone resection cut, will establish that same defined stability gap made available by the tibia and femoral stability gap preparation plate 10.

The final bone resection of the proximal surface of the tibia cutting guide arrangement 42 as part of the mounting arrangement between the final bone resection of the proximal surface of the tibia cutting guide arrangement 42 and the joint liner 37 includes a pair of lug extensions or protrusions 52, which are adapted to be slotted to the corresponding pair of slots 41 on the front side 40 of the joint liner 37.

FIG. 3f shows the final bone resection of the proximal surface of the tibia cutting guide arrangement 42 mounted to the joint liner 37 wherein the engagement between the lug extensions 52 of the final bone resection of the proximal surface of the tibia cutting guide arrangement 42 and that pair of slots 41 on the front side 40 on the joint liner 37 means that the indicator slot 51 of the cutting guide 50 aligns in the same orientation as the referenced plane of the underside 43 of the joint liner 37.

As it is to be envisaged the pair of slots 41 of the joint liner 37, before any height adjustments of tibia and femoral stability gap preparation plate 10 would be generally on the horizontal plane consistent with the initial resected surface 35 of the tibia shown in FIG. 3b.

None the less, as the height adjustment extension tabs 13, 14 and 15 of the tibia and femoral stability gap preparation plate 10 are adjusted to provide the stability gap this then alters the orientation of the underside 43 of the joint liner 37 and so to corresponding orientation of the slots 41 on the front side 40 of the joint liner 37.

Accordingly, as the pair of slots 41 of the joint liner 37 have now been offset through height adjustment of the tibia and femoral stability gap preparation plate 10 means that the corresponding lug extensions 52 of the final bone resection of the proximal surface of the tibia cutting guide arrangement 42 will also be offset so that the indicator slot 51 of the cutting guide 50 will represent the same reference plane that exists on the underside 43 of the joint liner 37.

This mounted engagement between the joint liner and the final bone resection of the proximal surface of the tibia cutting guide arrangement 42 shown in FIG. 3f provides for the first mounted position.

There is then the requirement to establish a second mounted position so that the cutting guide 50 and notably the correctly aligned indicator slot 50 now orientated the same as the reference plane on the underside 43 of the joint liner 37 can cut into a new layer of bone below the initial resected surface of the tibia.

Through the use of the vertical support mount 55 included a part of the final bone resection of the proximal surface of the tibia cutting guide arrangement 42, the cutting guide 50 can be incrementally adjusted vertically there along the vertical support mount 55 shown by way of arrows 57 in FIG. 3f.

The vertical adjustment of the cutting guide 50 as part of the final bone resection of the proximal surface of the cutting guide arrangement 42 can be achieved through conventional incremental adjustments, such as through a ratchet, gearing, use of cams and so forth.

Figure 3G:
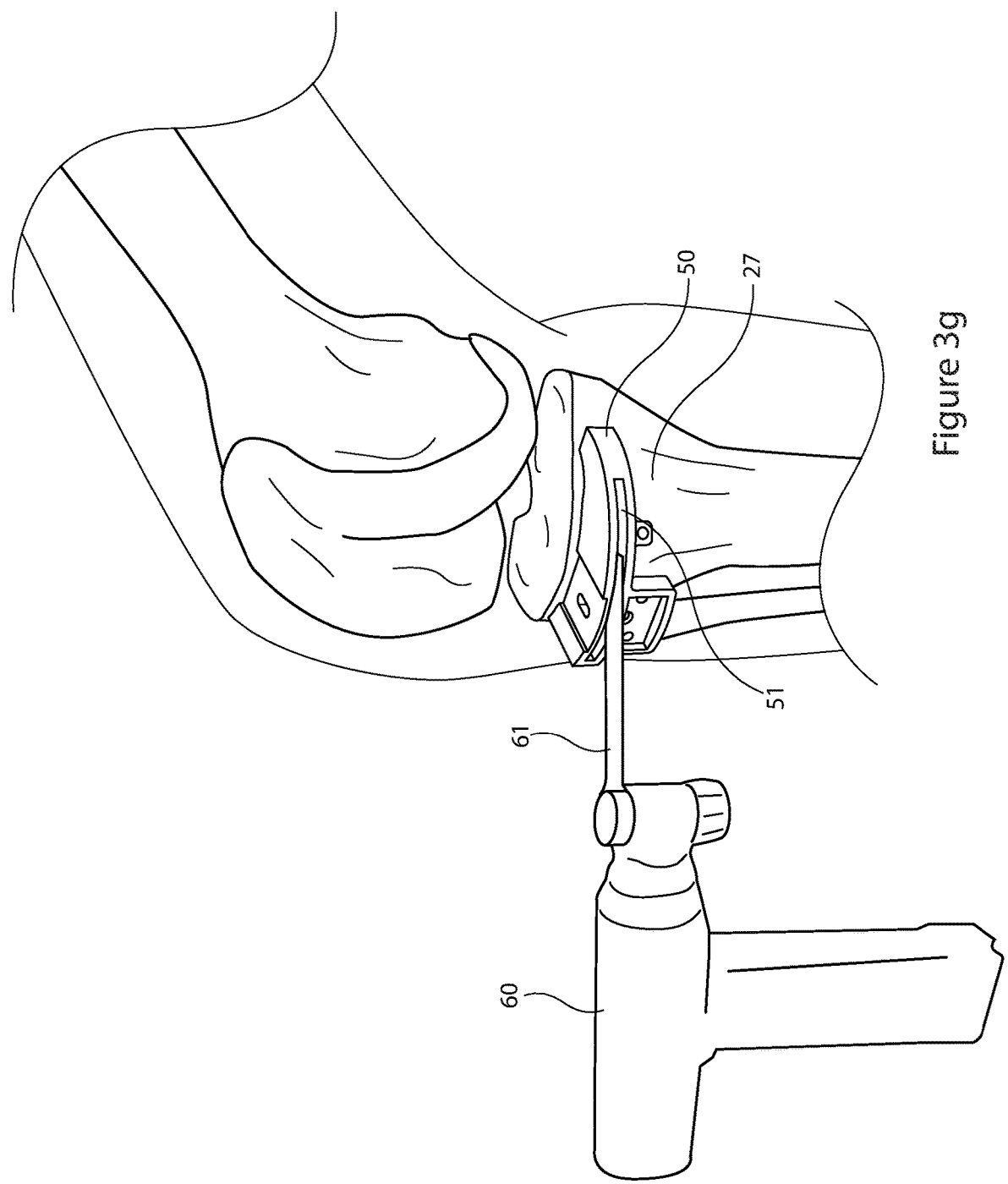

As seen in FIG. 3g once the cutting guide 50 has been lowered, the cutting guide 50 can then be separated from the final bone resection of the proximal surface of the tibia cutting guide arrangement 42. Wherein the vertical support 52 is also withdrawn.

Although the mounted means are not shown, the cutting guide 50 is mounted to the tibia 27 in the second mounted position which was provided for by the vertical support mount 55 included as part of the final bone resection of the proximal surface of the tibia cutting guide arrangement 42.

Hence, the second mounted position has the cutting guide 50 fastenable in the correct vertical position for cutting into new bone below the initial resected proximal surface 35 of the tibia 27 shown in FIG. 3b.

Also the indicator slot 51 for the correct orientation is aligned as the same reference plane established on the under side 43 of the joint liner 37. However, the practicalities of the final resection requires the main infrastructure of the final bone resection of the tibia cutting guide arrangement 42 to be withdrawn. So once the second mounted position has been established the cutting guide 50 as shown in FIG. 3f would be then mounted though various pins and or bolts (not shown) to the tibia 27.

The cutting guide 50 is mounted with the indicator slot 50 correctly aligned and at the appropriate depth below the initially resected proximal surface 35 of the tibia 27, as seen in FIG. 3g, wherein the blade or saw 61 of a handheld cutting implement 60 is guidable and orientated through the slot 51 to enable for a final bone resection providing a profile of the proximal surface of the tibia, shown as 70 in FIG. 3h the same as the reference plane, ensuring a stability gap so that the tibia component insert of the prosthetic knee (not shown) is stable and balanced throughout the arc of motion in the artificial knee joint (not shown) that one would expect from a normal healthy knee.

The invention claimed is:

1. An arrangement for preparation of a proximal surface of a tibia for a tibia component of a prosthetic knee joint, said arrangement including:
   a tibia and femoral stability gap preparation plate, said tibia and femoral stability gap preparation plate adapted to be placed upon an initially resected proximal surface of a tibia, said tibia and femoral stability gap preparation plate including an upper side, said upper side having a plurality of user operable height adjustable extension tabs;
   a joint liner, wherein each user operable height adjustable extension tab is adapted to engage said joint liner, wherein said joint liner further includes an upper articulated surface to engage a femoral component of a prosthetic knee joint, such that a height adjustment of said plurality of user operable height adjustable extension tabs creates a stability gap defined between the tibia and femoral stability gap preparation plate and the joint liner, wherein the stability gap is commensurate with a reference plane defined by an underside of the joint liner;

a tibia cutting guide assembly including a slot configured to act as a reference guide for cutting the tibia;

a mounting arrangement between said joint liner and said tibia cutting guide assembly, wherein said mounting arrangement is configured to provide a first mounted position between said joint liner and said tibia cutting guide assembly, wherein the slot is aligned with the reference plane; and said mounting arrangement further configured to provide a second mounted position wherein the slot aligned with the same reference plane of the underside of the joint liner is vertically below the first mounted position and below the initially resected proximal surface of the tibia.

2. The arrangement of claim 1 wherein a front side of the joint liner includes a pair of slots, and the tibia cutting guide assembly includes a pair of corresponding lugs.

3. The arrangement of claim 1 wherein the mounting arrangement includes a vertical support mount, wherein the vertical support mount allows the slot to be vertically adjustable there along said vertical support mount.

4. The arrangement of claim 3 wherein the vertical support mount is adapted to incrementally adjust and position the slot vertically there along said vertical support mount.

5. The arrangement of claim 4 wherein vertical incremental adjustment of the slot along the vertical support mount includes a ratchet arrangement, a clutch, gearing or cams.

6. The arrangement of claim 1 wherein the tibia and femoral gap preparation plate includes three user operable height adjustable extension tabs.

7. The arrangement of claim 1 wherein each user operable height adjustable extension tab is in communication with a corresponding user engageable knob.

8. The arrangement of claim 7 wherein each user operable height adjustable extension tab includes a mechanical, hydraulic, electrical, electronic or pneumatic drive action.

9. The arrangement of claim 1 further including a top plate restable on top of the plurality of user operable height adjustable extension tabs.

10. The arrangement of claim 1 wherein the joint liner includes a pair of lugs and the tibia cutting guide assembly includes a pair of corresponding slots.

* * * * *